(12) United States Patent
Jefferis et al.

(10) Patent No.: US 10,098,749 B2
(45) Date of Patent: Oct. 16, 2018

(54) PROXIMAL INTERPHALANGEAL JOINT PROTHESIS

(71) Applicants: Ryan A. Jefferis, Cleveland Heights, OH (US); Michelle A. Chin, Washington, DC (US); Robert (aka Andrew) A. Fields, Memphis, TN (US)

(72) Inventors: Ryan A. Jefferis, Cleveland Heights, OH (US); Michelle A. Chin, Washington, DC (US); Robert (aka Andrew) A. Fields, Memphis, TN (US)

( * ) Notice: Subject to any disclaimer, the term of this patent is extended or adjusted under 35 U.S.C. 154(b) by 36 days.

(21) Appl. No.: 15/222,327

(22) Filed: Jul. 28, 2016

(65) Prior Publication Data
US 2017/0027710 A1 Feb. 2, 2017

Related U.S. Application Data

(60) Provisional application No. 62/199,307, filed on Jul. 31, 2015.

(51) Int. Cl.
*A61F 2/42* (2006.01)
*A61F 2/30* (2006.01)

(52) U.S. Cl.
CPC ........ *A61F 2/4241* (2013.01); *A61F 2/30771* (2013.01); *A61F 2/30942* (2013.01);
(Continued)

(58) Field of Classification Search
CPC ............ A61F 2/4241; A61F 2002/4243; A61F 2002/4246; A61F 2002/4235; A61F 2002/4228
See application file for complete search history.

(56) References Cited

U.S. PATENT DOCUMENTS 3,462,765 A 8/1969 Swanson
3,506,982 A 4/1970 Steffee
(Continued)

FOREIGN PATENT DOCUMENTS

EP 1203569 A1 5/2002

OTHER PUBLICATIONS

Brannon et al, Experience with a Finger-Joing Prosthesis, The Journal of Bone and Joint Surgery, American, 1959, vol. 41-A(1); pp. 87-102.
(Continued)

*Primary Examiner* — Jason-Dennis Stewart
(74) *Attorney, Agent, or Firm* — Robert A. Jefferis; Daugherty & Del Zoppo Co., LPA

(57) ABSTRACT

An interphalangeal prosthesis (10) includes a mobile element (12), a proximal fixation element (22), and a distal fixation element (24). The mobile element (12) includes a proximal portion (42, 62, 94) and a distal portion (43, 64, 92), and the proximal portion includes three proximal mobile coupling contiguous surfaces (46, 48, 50) and a proximal mobile coupling protrusion (52), and the distal portion includes a distal coupling mobile surface (54) and a distal mobile coupling protrusion (56), and the proximal portion and the distal portion move relative to each other primarily in an axis of rotation perpendicular to a plane that extends through the proximal mobile coupling protrusion, the three proximal mobile coupling contiguous surfaces, the distal coupling mobile surface, and the distal mobile coupling protrusion in an implanted configuration. The proximal fixation element (22) couples to the three proximal mobile coupling contiguous surfaces and the proximal mobile coupling protrusion of proximal portion, and couples to a joint bone surface and a bone canal. The distal fixation element (24) couples to the distal coupling mobile surface
(Continued)

and the distal mobile coupling protrusion, and couples to an opposing joint bone surface and a second bone canal.

17 Claims, 9 Drawing Sheets

(52) U.S. Cl.
CPC .. *A61F 2/4225* (2013.01); *A61F 2002/30069* (2013.01); *A61F 2002/3092* (2013.01); *A61F 2002/30448* (2013.01); *A61F 2002/30624* (2013.01); *A61F 2002/30878* (2013.01); *A61F 2002/30884* (2013.01); *A61F 2002/30962* (2013.01); *A61F 2002/4228* (2013.01); *A61F 2002/4248* (2013.01); *A61F 2240/001* (2013.01); *A61F 2310/00023* (2013.01); *A61F 2310/00029* (2013.01)

(56) References Cited

U.S. PATENT DOCUMENTS

| | | |
|---|---|---|
| 3,593,342 A | 7/1971 | Niebauer |
| 3,651,521 A | 3/1972 | Devas |
| 3,739,403 A | 6/1973 | Nicolle |
| 3,760,427 A | 9/1973 | Schultz |
| 3,805,302 A | 4/1974 | Mathys |
| 3,875,594 A | 4/1975 | Swanson |
| 3,899,796 A | 8/1975 | Gschwend et al. |
| 3,946,445 A | 3/1976 | Bentley et al. |
| 3,990,118 A | 11/1976 | Strickland et al. |
| 3,991,425 A | 11/1976 | Martin et al. |
| 4,011,603 A | 3/1977 | Steffee |
| 4,059,854 A | 11/1977 | Laure |
| 4,131,957 A | 1/1979 | Bokros |
| 4,150,444 A | 4/1979 | Hagert |
| 4,193,139 A | 3/1980 | Walker |
| 4,231,121 A | 11/1980 | Lewis |
| 4,242,759 A | 1/1981 | White |
| 4,304,011 A | 12/1981 | Whelan, III |
| 4,349,922 A | 9/1982 | Agee |
| 4,352,212 A | 10/1982 | Greene et al. |
| 4,759,768 A | 7/1988 | Hermann et al. |
| 5,007,932 A | 4/1991 | Bekki et al. |
| 5,011,497 A | 4/1991 | Persson |
| 5,047,059 A | 9/1991 | Saffar |
| 5,092,896 A | 3/1992 | Meuli et al. |
| 5,133,761 A | 7/1992 | Krouskop |
| 5,147,386 A | 9/1992 | Carignan et al. |
| 5,290,314 A | 3/1994 | Koch et al. |
| 5,314,486 A | 5/1994 | Zang et al. |
| 5,405,401 A | 4/1995 | Lippincott, III et al. |
| 5,458,647 A | 10/1995 | Brochier et al. |
| 5,522,903 A | 6/1996 | Sokolow et al. |
| 5,674,297 A | 10/1997 | Lane et al. |
| 5,702,471 A | 12/1997 | Grundei et al. |
| 5,728,163 A | 3/1998 | Maksene |
| 5,776,202 A | 7/1998 | Copf et al. |
| 5,782,927 A | 7/1998 | Klawitter et al. |
| 5,984,971 A | 11/1999 | Faccioli et al. |
| 6,051,751 A | 4/2000 | Sioshansi et al. |
| 6,059,832 A * | 5/2000 | Menon ............... A61B 17/15 623/21.15 |
| 6,099,571 A | 8/2000 | Knapp |
| 6,159,247 A | 12/2000 | Klawitter et al. |
| 6,342,076 B1 | 1/2002 | Lundborg |
| 6,352,560 B1 | 3/2002 | Poeschmann et al. |
| 6,423,097 B2 | 7/2002 | Rauscher |
| 6,454,808 B1 | 9/2002 | Masada |
| 6,682,565 B1 | 1/2004 | Krishnan |
| D490,900 S | 6/2004 | Ogilvie |
| 8,303,666 B2 | 11/2012 | Vanasse |
| 8,449,620 B2 | 5/2013 | Hakansson et al. |
| 8,491,663 B2 | 7/2013 | Lindner et al. |
| 8,740,986 B2 | 6/2014 | Link |
| 8,858,644 B2 | 10/2014 | Goubau et al. |
| 2003/0040805 A1 | 2/2003 | Minamikawa |
| 2004/0102853 A1 | 5/2004 | Boumann et al. |
| 2008/0154385 A1* | 6/2008 | Trail ................. A61F 2/4241 623/21.15 |
| 2011/0106269 A1* | 5/2011 | Warburton ............ A61B 17/15 623/21.15 |
| 2011/0184527 A1* | 7/2011 | Vanasse ................ A61F 2/42 623/21.15 |
| 2011/0257755 A1* | 10/2011 | Bellemere ............ A61F 2/4241 623/21.15 |
| 2014/0025181 A1* | 1/2014 | Vanasse ................. A61F 2/28 623/23.55 |

OTHER PUBLICATIONS

Reis et al., Integral Hinge Joint, Annals of Rheumatic Diseases, 1969, vol. 28, supplement, p. 59-62.
Griffiths et al., Three years' experience of metacarpophalangeal joint replacement in the rheumatoid hand, The Hand, Oct. 1975, vol. 7, issue 3, pp. 275-283, abstract.
Doi et al., Alumina ceramic finger implants: A preliminary biomaterial and clinical evaluation, The Journal of hand Surgery, Sep. 1984, vol. 9, issue 5, pp. 740-749, abstract.

* cited by examiner

Figure 5A  Figure 5B

PROXIMAL INTERPHALANGEAL JOINT PROTHESIS

FIELD OF THE INVENTION

The following generally relates to interphalangeal joint replacement, and is described with particular application to a proximal interphalangeal (PIP) joint replacement apparatus and method of construction.

BACKGROUND OF THE INVENTION

PIP joints, such as those of the hands or feet, can be damaged by trauma, injury and/or by disease such as osteoarthritis, such that the joint is no longer viable. PIP joints differ from other joints in that the range of motion occurs generally within a single plane, e.g. flexion without significant lateral rotation that occurs with other joints, such as with a shoulder or a hip. A healthy range of motion includes 0-5 degrees in extension to 100-115 degrees in flexion. A functional range of motion is 36-86 degrees in flexion, and an acceptable outcome for PIP arthroplasty is 50-70 degrees in flexion.

Existing replacement joints or prostheses typically are integrated devices which includes an affixed attachment mechanism glued and/or located in a medullary canal of the bone. The opposing faces of the bones, such as ends of the phalanges are removed to create a stable supporting surface through which an opening is made into the medullary canal parallel to the length of the bone. Deformities in the bone are also typically removed. Direct attachment of the replacement joint to the bone makes revision, i.e. replacement of the prosthesis, in instances of replacement joint failure difficult and can further damage the surrounding tissue.

Due to the stresses placed on the joint, insufficient lateral stability, and expected implant survival rates, one alternative approach to PIP replacement is to fuse the joint rather than replace the joint. This is often the procedure for younger patients, which have expected survival rates beyond what is currently offered in replacement joints. Patient satisfaction with current prostheses is considerably less than hip and knee arthroplasties. PIP arthroplasties are typically used to alleviate debilitating joint pain and/or deformity. Current approaches are moderately successful in alleviating pain and restoring cosmetic appearance, but are prone to failure and maintain only a nominal range of motion.

Arthroplasties are typically planned prior to a replacement with a specific range of replacement sizes ordered in advance, and the replacement joint selected based on external measurements, medical imaging, and external visual observation. Tissue damage including both the bone and surrounding tissue can be difficult to assess prior to the operative procedure. Soft tissues play a considerable role in lateral support of interphalangeal joints. Prostheses are manufactured according to various sizes and the range of sizes limited by cost, e.g. more sizes available to choose from means more devices produced than needed, and fewer sizes are limited by proper functioning of the prostheses in terms of range of motion, gripping strength, lateral stability, etc.

Dissatisfaction with existing PIP replacement joints includes failure due to mechanical failure, dislocation, and/or limited range of motion. Mechanical failures, such as fracturing of the implanted joint, can occur due to repetitive motion and stresses placed on the joint. Dislocation occurs where the connection between an attachment mechanism of the replacement joint and a canal in the bone tissue dislocate or separate. The dislocation can include a loosening of the replacement joint and migration in the canal of the bone. The loosening and migration can further damage surrounding tissue and affect continued viability of the joint operation.

SUMMARY OF THE INVENTION

Aspects described herein address the above-referenced problems and others.

The following describes a modular prosthesis which can be assembled intraoperatively with proximal and distal fixation elements coupled to a mobile element. The fixation element facilitates osseointegration, and couples with the mobile element. The mobile element can include one of a constrained mobile element, a partially constrained mobile element, or an unconstrained mobile element. In some embodiments, the fixation elements and/or the mobile elements are constructed using three dimensional printing techniques. In some embodiments, the fixation elements and/or mobile elements are scaled according to each patient.

In one aspect, an interphalangeal prosthesis includes a mobile element, a proximal fixation element, and a distal fixation element. The mobile element includes a proximal portion and a distal portion, and the proximal portion includes three proximal mobile coupling contiguous surfaces and a proximal mobile coupling protrusion, and the distal portion includes a distal coupling mobile surface and a distal mobile coupling protrusion, and the proximal portion and the distal portion are configured to move relative to each other primarily in an axis of rotation perpendicular to a plane that extends through the proximal mobile coupling protrusion, the three proximal mobile coupling contiguous surfaces, distal coupling mobile surface, and the distal mobile coupling protrusion in an implanted configuration. The proximal fixation element couples to the three proximal mobile coupling contiguous surfaces and the proximal mobile coupling protrusion of proximal portion, and configured to couple to a joint bone surface and a bone canal. The distal fixation element couples to the distal mobile coupling surface and the distal mobile coupling protrusion, and configured to couple to an opposing joint bone surface and a second bone canal.

In another aspect, an interphalangeal prosthesis includes a mobile element, a proximal fixation element, and a distal fixation element. The mobile element includes a proximal portion and a distal portion, and the proximal portion includes three proximal mobile coupling contiguous surfaces and a proximal mobile coupling protrusion, and the distal portion includes a distal coupling mobile surface and a distal mobile coupling protrusion, and the proximal portion and the distal portion are configured to move relative to each other primarily in an axis of rotation perpendicular to a plane that extends through the proximal mobile coupling protrusion, the three proximal mobile coupling contiguous surfaces, distal coupling mobile surface, and the distal mobile coupling protrusion in an implanted configuration. The proximal fixation element couples to the three proximal mobile coupling contiguous surfaces and the proximal mobile coupling protrusion of proximal portion, and configured to couple to a joint bone surface and a bone canal. The distal fixation element couples to the distal coupling mobile surface and the distal mobile coupling protrusion, and configured to couple to an opposing joint bone surface and a second bone canal. At least one of the mobile element, the proximal fixation element, or the distal fixation element is formed using three dimensional (3D) printing.

In another aspect, a method for constructing an interphalangeal prosthesis includes printing in three dimensions (3D) at least one of a mobile element, a proximal fixation element, and/or a distal fixation element according to received dimensions of interphalangeal bones.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIGS. 5A-5D schematically illustrate an example modular PIP prosthesis distal fixation element in different views.

DETAILED DESCRIPTION OF EMBODIMENTS

Figure 1:
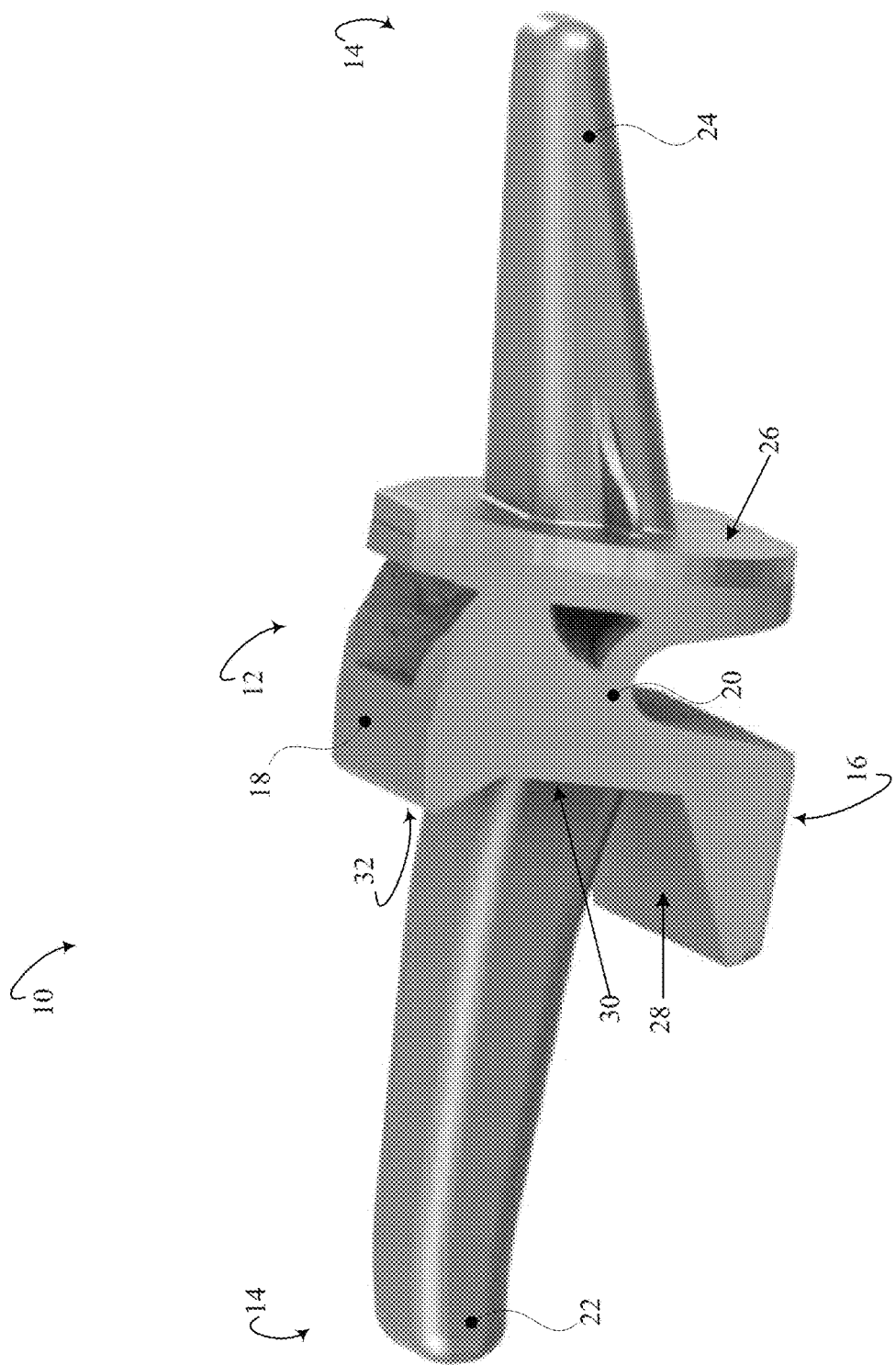
FIG. 1 schematically illustrates an example modular PIP prosthesis in a perspective view with a mobile element coupled to fixation elements.

Initially referring to FIG. 1, an example modular PIP prosthesis 10 in a perspective view with a mobile element 12 coupled to fixation elements 14 is schematically illustrated. The modular PIP prosthesis 10 is manufactured from one or more biocompatible materials. The view of the modular PIP prosthesis 10 is oriented with palmar surfaces 16, i.e. facing the same direction as palm of the hand, and dorsal surfaces 18, i.e. facing the same direction as the back of the hand. The mobile element 12 includes a constrained mobile element 20. The modular PIP prosthesis 10 includes fixation elements 14 which are coupled to the constrained mobile element 12. The mobile element 12 can include an unconstrained element or a partially constrained element. The mobile element 12 can be selected intraoperatively from the unconstrained, partially constrained, and constrained mobile elements. In some instances, the selection can be guided by a state of soft tissue. For example, an unconstrained mobile element is selected for healthy soft tissue, such as in a younger person, replacement of a joint damaged by trauma, and the like. In another example, a constrained mobile element is selected for soft tissue which is unlikely to support unconstrained movement, such as damaged collateral ligaments.

The fixation elements 14 include a proximal fixation element 22 and a distal fixation element 24. The fixation elements 14 are formed of materials and surfaces which promote osseointegration, i.e. bone growth into the fixation element. The fixation elements are inserted into the medullary canal. No barrier forming material, such as an epoxy adhesive, is used to affix the fixation elements 14 because it will interfere with osseointegration. In some instances, the osseointegration prevents pistoning movement of the fixation element in the medullary canal which can damage bone tissue. The proximal fixation element 22 is inserted into an opening of the medullary canal of the proximal phalange, and the distal fixation element 24 is inserted into an opening of the medullary canal of the middle phalange. These openings are formed by cuts to bone using techniques known in the art.

The proximal fixation element 22 includes three proximal fixation surfaces 28, 30, 32 which couple to a bone surface of the proximal phalange and transmit forces to the bone surface. The distal fixation element 24 includes a distal fixation surface 26 which couples to a bone surface of the distal phalange and transmits forces to the bone surface. A jig (not shown) can be used to remove the bone faces of the phalanges, e.g. one cut to middle phalange, three cuts to proximal phalange. In some instances, the jig provides a more consistent and precise match to the fixation elements 14. The fixation elements 14 are sized to and inserted to a depth less than or equal fifty to percent (≤50%) of the length of the medullary canal. For example, in a medullary canal of 45 mm, a length of 20 mm is used, or for a medullary canal length of 30 mm, a length of 15 mm is used.

In one embodiment, at least one of the mobile element 12 and the fixation elements 14 are constructed using three dimensional printing (3D). The 3D printing can include printing metal based components. In one embodiment, sizes based on the bone end diameter include fours sizes, e.g. small (S), medium (M), large (L), and extra large (XL) for each of the fixation elements and mobile which can be mixed, e.g. L for proximal fixation element 22, M for distal fixation element 24. In another embodiment, the mobile element 12 and the fixation elements 14 can be sized according to an anatomical image of the subject, e.g. a Computer Tomography (CT) image, a Magnetic Resonance Image (MRI), and the like, or scaled to a commercially available three dimensional anatomical atlas corresponding the dimensions of the subject.

In one embodiment, the mobile element 12 is coupled to the fixation elements 14 using a pressure fit. In one embodiment, the mobile element 12 is coupled to the fixation elements using a biocompatible adhesive, such as cyanoacrylate-based adhesives.

Figure 2:
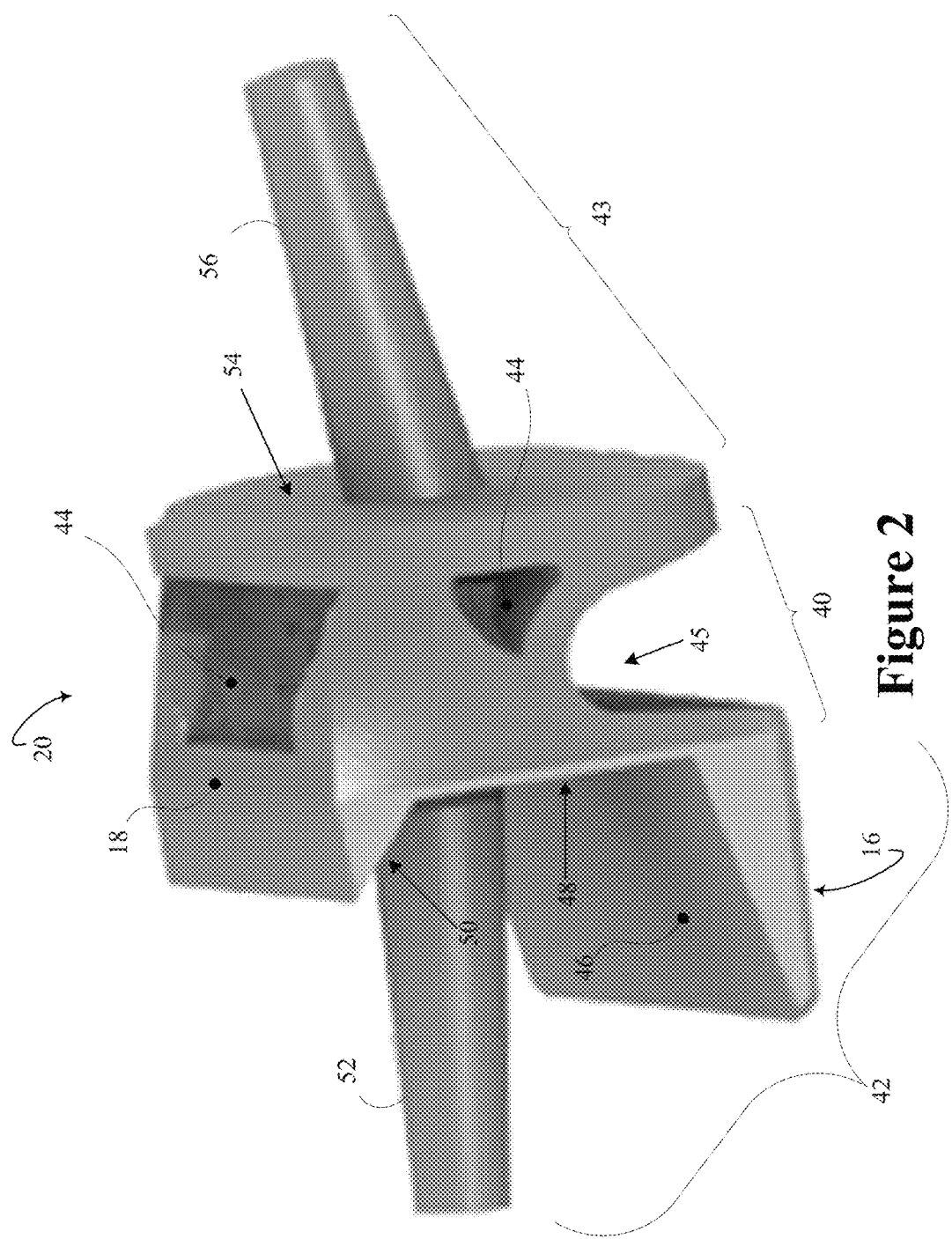
FIG. 2 schematically illustrates an example modular PIP prosthesis constrained mobile element in a perspective view.

With reference to FIG. 2, an example modular PIP prosthesis constrained mobile element 20 is schematically illustrated in a perspective view. The constrained mobile element 20 comprises a single integrated apparatus with three portions: a central portion 40, a proximal portion 42, and a distal portion 43. The constrained mobile element 20 is constructed using structural topological optimization (STO), such as described in Topology Optimization: Theory, Methods, and Applications (M. Bendsoe et al. 2003), which identifies material necessary to operate the integrated hinge shape and removes one or more areas 44 of structurally unnecessary material. In some instances, the removed areas 44 of material prevent potential fractures of the material due to stress and wear of the joint after implantation. The removed areas can include portions of the distal faces, lateral faces, and/or dorsal faces.

The constrained mobile element 20 can be manufactured of a medical grade elastomer, such as silicone, polyolefin, natural, and styrene-butadiene rubbers. The STO uses a center of rotation approximately aligned with a center of a proximal head of the proximal phalange in a sagittal plane and located more proximally than the joint center of an average healthy PIP joint.

The central portion 40 includes a u-shape slot 45 facing the palmar surface and providing for flexion of the PIP modular prosthesis by compression of surfaces on each side of the u-shape slot 45. Lateral and dorsal surfaces are formed to the outer dimensions of a healthy joint and to couple with the fixation elements 14. In some instances, the outer dimensions provide an improved cosmetic appearance to the joint.

The proximal portion 42 includes three proximal surfaces, a first proximal mobile surface 46, a second proximal mobile surface 48, a third proximal mobile surface 50, and a proximal mobile coupling protrusion 52 which couple to complementary surfaces and an opening of the proximal fixation element 76. The three proximal mobile surfaces 46, 48, 50 are contiguous and increase the surface area to the proximal fixation element 22 which in turn increases the surface area to the proximal phalange for forces acting between the proximal phalange and the modular PIP prosthesis 10. In some instances, the first proximal mobile surface 46 located palmar and the third proximal mobile surface 50 located dorsal provide anti-rotation support for the mobile element 12.

The proximal mobile coupling protrusion 52 can include a cylindrical taper dimensioned to be received within the opening of the proximal fixation element 76. In other embodiments, the proximal mobile protrusion 52 can include a cruciform or "+" shape, octagonal shape, hexagonal shape, pyramidal shape, and the like. The proximal mobile coupling protrusion 52 can project from the second proximal surface 48 at an angle which follows the natural orientation of the medullary canal of the proximal phalange, such as approximately 10 degrees.

The distal portion 43 includes a distal mobile surface 54 and a distal mobile coupling protrusion 56 which couple to a complementary surface and an opening of the distal fixation element 82. In other embodiments, the distal mobile protrusion 56 can include a cruciform or "+" shape, octagonal shape, hexagonal shape, pyramidal shape, and the like. The distal mobile coupling protrusion 56 can project from the distal mobile surface 54 at an angle which follows the natural orientation of the medullary canal of the middle phalange, such as approximately 10 degrees.

Figure 3A:
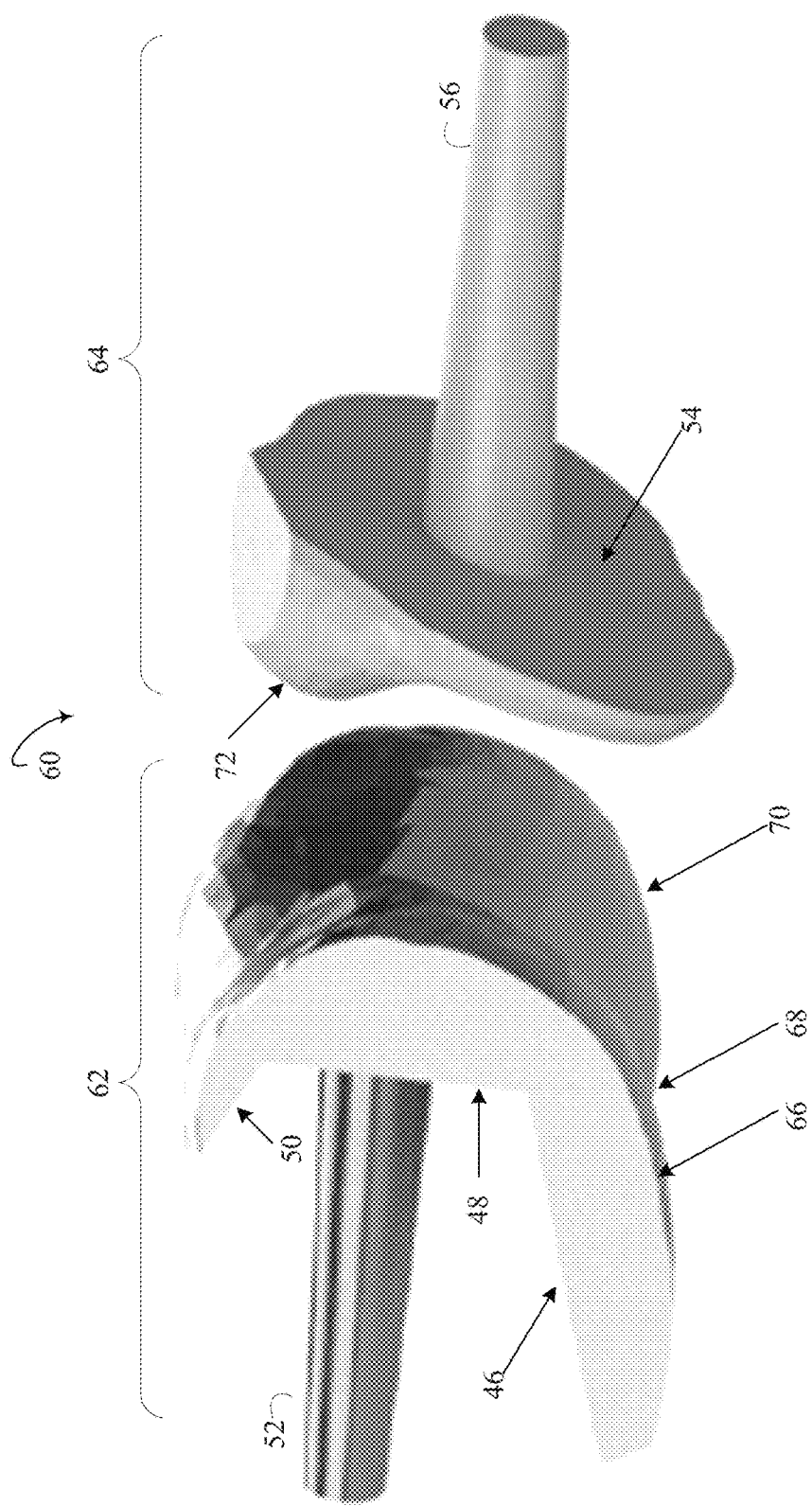
FIGS. 3A-3C schematically illustrate an example modular PIP prosthesis unconstrained mobile element in different views.
Figure 3B:
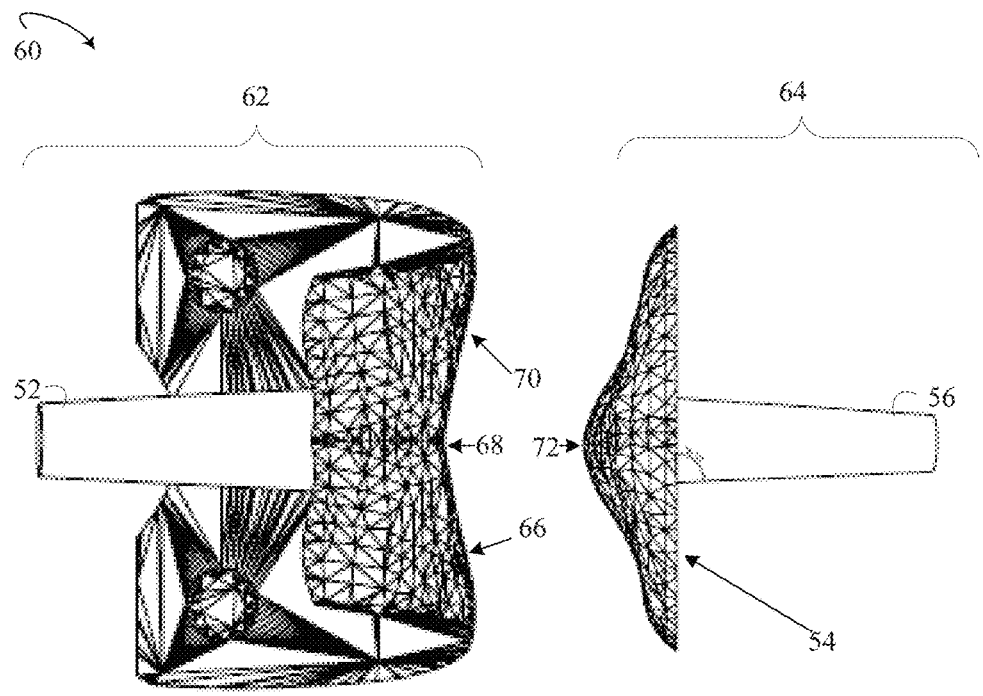

With reference to FIG. 3A, an example modular PIP prosthesis unconstrained mobile element 60 in a perspective view is schematically illustrated. FIG. 3B illustrates the example modular PIP prosthesis unconstrained mobile element 60 in a dorsal view, and FIG. 3C in a side or lateral view. The unconstrained mobile element 60 includes a proximal portion 62 and a distal portion 64. The proximal portion 62 and the distal portion 64 are physically separated. The proximal portion 62 and the distal portion 64 are constructed based on an image of a healthy subject PIP joint, scaled anatomical atlas, average of healthy subject PIP joints, and the like. The opposing surfaces of proximal portion 62 and the distal portion 64 which function as the joint can be smoothed.

The proximal portion 62 of the unconstrained mobile element 60 includes the three mobile coupling surfaces 46, 48, 50 and proximal mobile coupling protrusion 52 in the same dimensions as the proximal portion of the unconstrained mobile element 20. The same dimensions can facilitate the selection of the mobile element 10 intraoperatively and couple interchangeably to the proximal fixation element 22. The opposing surface to the distal portion 64 includes two joint surfaces 66, 70 which form a center depression 68. The center depression 68 is formed from the dorsal edge to the palmar edge of the two joint surfaces 66, 70. The two joint surfaces 66, 70 are raised laterally which represent the condyles of the head of the proximal phalange and can provide a guided movement of the joint. The proximal portion 62 is comprised of a wear resistant material, such as cobalt-chromium (CoCr).

The distal portion 64 of the unconstrained mobile element 60 includes the coupling mobile surface 54 and distal mobile coupling protrusion 56 in the same dimensions as the distal portion of the unconstrained mobile element 20. The distal portion 64 is of a different wear resistant material, such as ultra high molecular weight polyethylene (UHMWPE), than the proximal portion 62, which reduces wear particles and increases device lifespan. The UHMWPE includes heavily cross linked polymer structures which are resistant to abrasion by the opposing surfaces of the proximal portion 62.

The distal portion 64 includes a joint surface with raised center ridge 72 running approximately dorsal to palmer which can represent the surface of a head of a middle phalange and can provide guided movement with the center depression 68 of the proximal portion 62. The raised center ridge 72 includes a depression or lessening in the ridge between the dorsal and palmer ends which in some instances keeps the distal portion 64 centered against the joint surfaces 66, 68 of proximal portion 62 during flexion and extension of the joint aided by soft tissue support.

The proximal portion 62 can be manufactured to maintain the radius of the joint surfaces 66, 68 while changing sizes of the distal portion 64 which can provide additional sizes. For example, with four sizes of a proximal portion 62, such as S, M, L, XL and with four sizes of a distal portion 64, such as S, M, L, XL, 16 different size combinations can be achieved, S-S, S-M, S-L, S-XL, M-S, M-M, M-L, M-XL, L-S, etc. In one embodiment, this is likely to include size combinations with the mobile element 12.

Figure 3C:
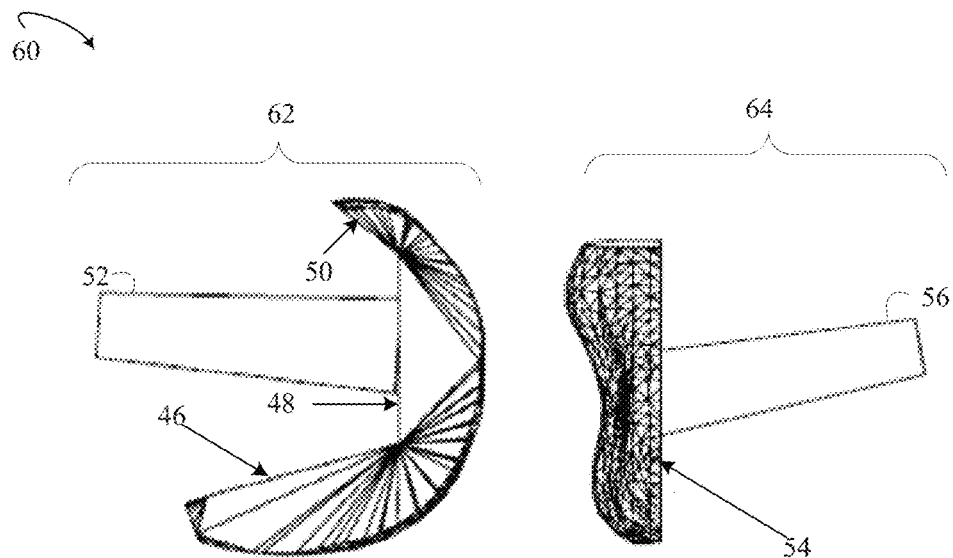

The side view of FIG. 3C includes a plane that extends through and includes the proximal mobile coupling protrusion 52 and the distal mobile coupling protrusion 56 each coupled to a corresponding protrusion of the fixation elements 14 in an implanted configuration. The axis of rotation of the implanted modular PIP prosthesis 10 is perpendicular to the plane.

With reference to FIGS. 4A-4D an example modular PIP prosthesis proximal fixation element 22 in a proximal facing view, a distal facing view, a side view, and a dorsal view respectively is schematically illustrated. The proximal fixation element 22 is manufactured of a biocompatible material, which promotes osseointegration, such as titanium or titanium-vanadium-aluminum alloys. In one embodiment cobalt-chromium is chosen as the material to counteract possible metal on metal wear with modular component 62 of which surface 46, 48, 50, and 52 are in contact. In one embodiment, the material of the proximal fixation element 22 is matched to the proximal portion 62 of the unconstrained mobile element 60.

Figure 4A:
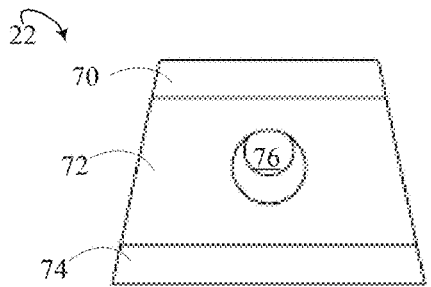
FIGS. 4A-4D schematically illustrate an example modular PIP prosthesis proximal fixation element in different views.

In FIG. 4A, the proximal view of the distal end of the proximal fixation element 22 illustrates a first coupling fixation surface 70, a second coupling fixation surface 72, and a third coupling fixation surface which are contiguous and configured to couple to the three coupling mobile surfaces 46, 48, 50 of the proximal portion of the mobile element 12. The second coupling fixation surface 72 includes an opening 76 which is dimensioned to receive and receives the proximal mobile protrusion 52 of the proximal portion of the mobile element 12. In one embodiment, the opening 76 includes a tapered cylindrical opening tapering down away from the opening 76 inside the proximal fixation protrusion 78. The opening 76 is enclosed opposite the second coupling fixation surface 72. In one embodiment the tapered opening includes a flange or flaring at the end. In one embodiment, the opening includes a cruciform shape complementary to a cruciform shape of the proximal mobile protrusion 52 of the mobile element 12.

Figure 4B:
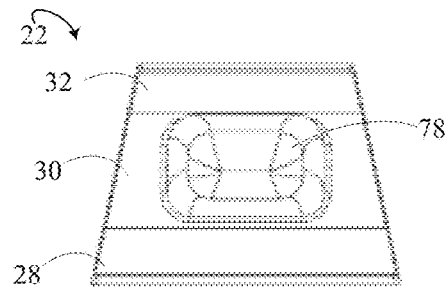
Figure 4C:
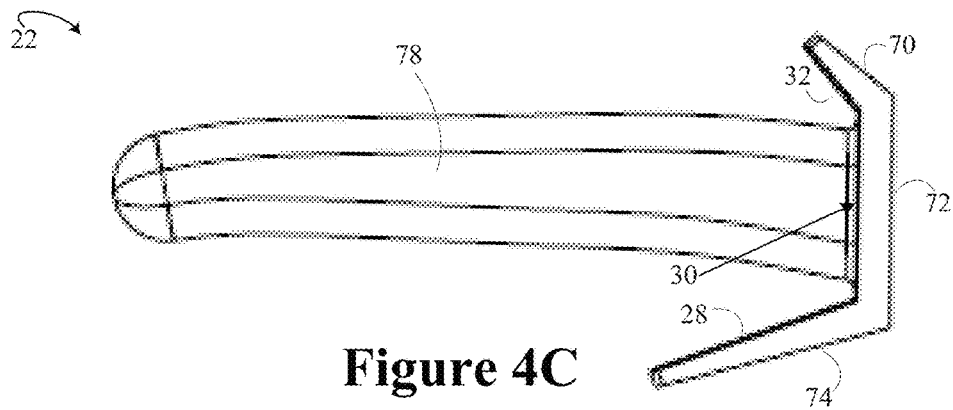
Figure 4D:
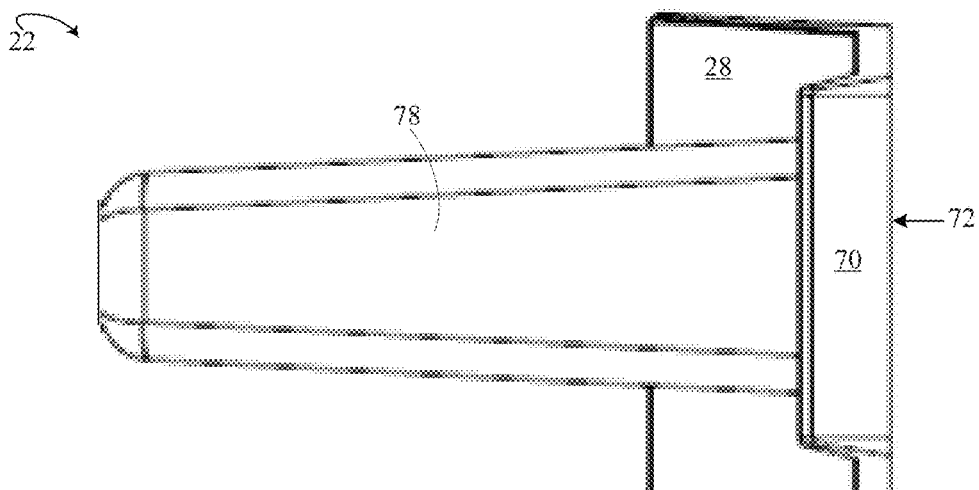

With reference to FIG. 4B, the three fixation surfaces 28, 30, 32 which affix and/or couple to a bone surface of the proximal phalange and transmit forces to the proximal bone surface are shown. The surfaces represent an approximate surface area of 115 mm$^2$, which varies with the size in a ratio of the first proximal surface 28: second proximal surface 30: third proximal surface 32 of 40:15:11. The first proximal fixation surface 28 and the third proximal fixation surface 32 are angled as illustrated in FIG. 4C from the second proximal fixation surface 30 away from the joint and toward the proximal phalange (as implanted) approximately 110 degrees and 140 degrees respectively. In one embodiment, the three proximal fixation surfaces 28, 30, 32 include a surface roughening to promote osseointegration, such as a titanium plasma spray (TPS). For example, a TPS spray of 30% porosity, 150 micron pore size, and a coating thickness of 1 mm provides a roughened surface.

A proximal fixation protrusion 78 of the proximal fixation element 22 includes a rectangular structure with rounded edges and a taper from the second proximal fixation surface 30 to an end opposite. The end opposite includes a rounded ovular end as illustrate in FIGS. 4C and 4D in a side view and dorsal/top view respectively. The proximal fixation protrusion 78 includes a slight curvature which approximates the curvature of the medullary canal. In some instances, the rounded rectangular shape provides resistance to torsional rotation. In some instances, the shape and materials of the proximal fixation element 22 provide good conditions for osseointegration, and load bearing ends.

Figure 5C:
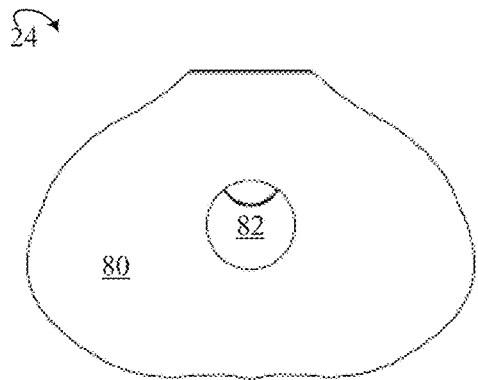
Figure 5C:
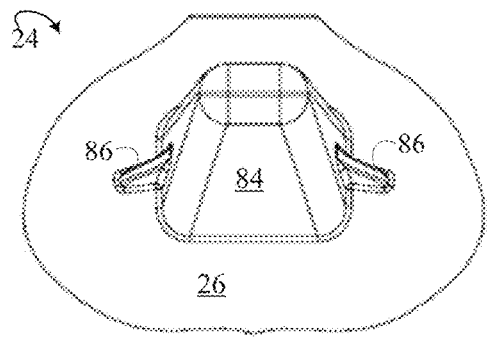
Figure 5C:
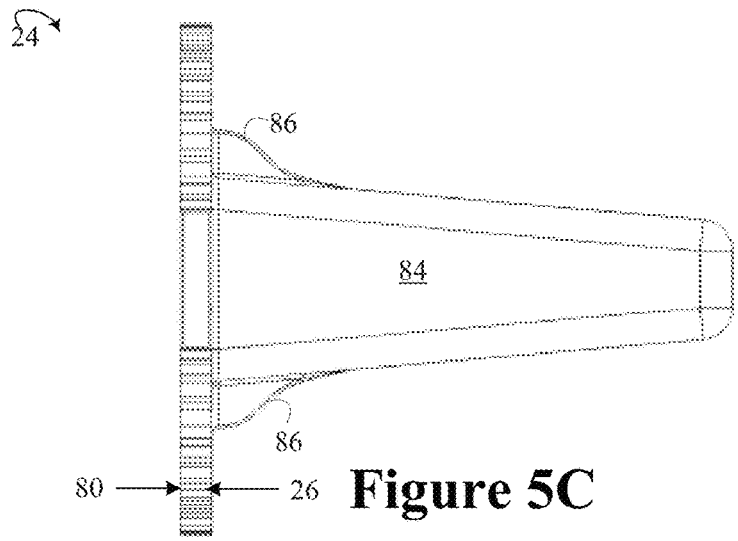

With reference to FIGS. 5A-5D, an example modular PIP prosthesis distal fixation element 24 is schematically illustrated in a distal facing view, a proximal facing view, a dorsal view, and a side view respectively. The distal fixation element 24 is manufactured of a biocompatible material that promotes osseointegration and of a different biocompatible material than the proximal fixation element, such as titanium. With reference to FIG. 5A, the distal fixation element 24 includes a distal fixation coupling surface 80 and an opening 82 is dimensioned to receive and couple to the distal mobile surface 54 and distal mobile protrusion 56 of the mobile element 12. In one embodiment, the opening 82 includes a tapered cylindrical opening. In one embodiment, the tapered cylindrical opening includes a flange or flaring at the end of the opening opposite the distal coupling surface 80. In one embodiment, the opening 82 includes a cruciform shape. The edges of the distal coupling surface 80 are dimensioned based on the cut surface of a head of the middle phalange and the outer dimensions of the distal mobile surface 54 of the mobile element 12.

With reference to FIG. 5B, the distal fixation surface 26 which affixes and/or couples to a bone surface of the distal phalange and transmits forces to the bone surface is shown with a distal fixation protrusion 84 of the distal fixation element 24. In one embodiment, the distal fixation surface is roughened to promote osseointegration. For example, using grit blasting, such as with 25 micron diameter average TiO$_2$ particles, a 1-2 micron roughened surface can be achieved. The surfaces of the proximal fixation protrusion 78 of the proximal fixation element 22 and the surfaces of the distal fixation protrusion 84 of the distal fixation element 24 are not roughened, which in some instances avoids stress shielding of the fixation elements 14.

Figure 5D:
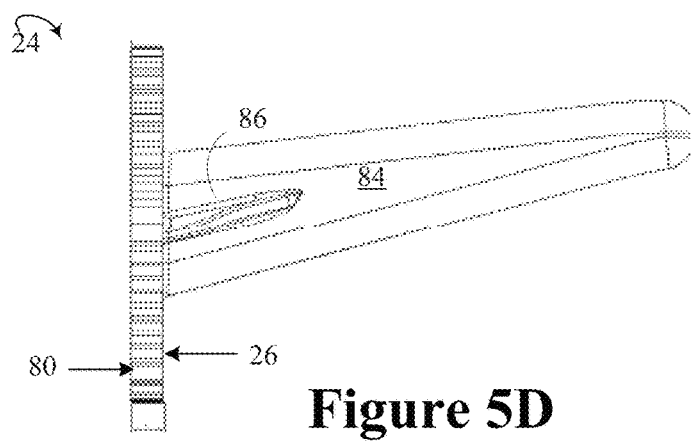
Figure 6A:
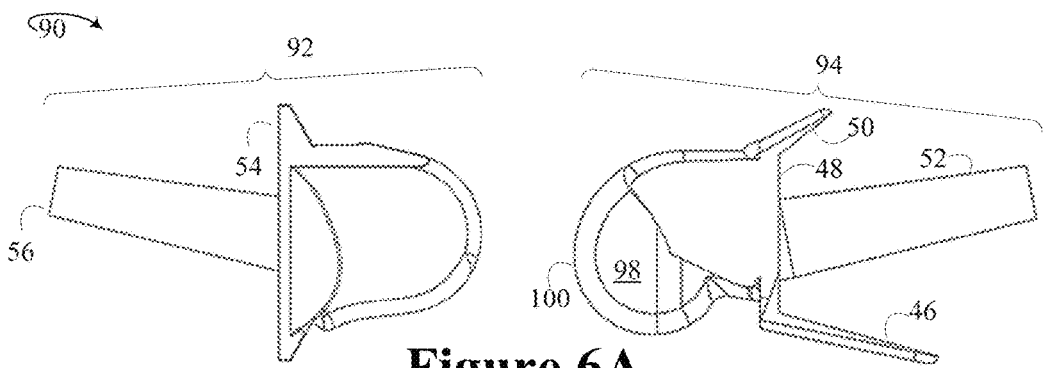
FIGS. 6A-6E schematically illustrate an example modular PIP prosthesis partially constrained mobile element in different views FIG. 7 flowcharts an embodiment of constructing a modular PIP prosthesis.
Figure 6B:
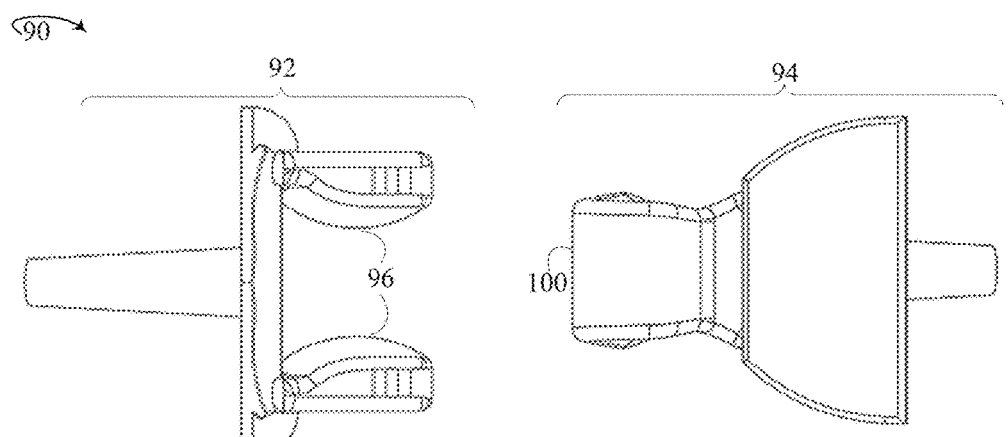
Figure 6C:
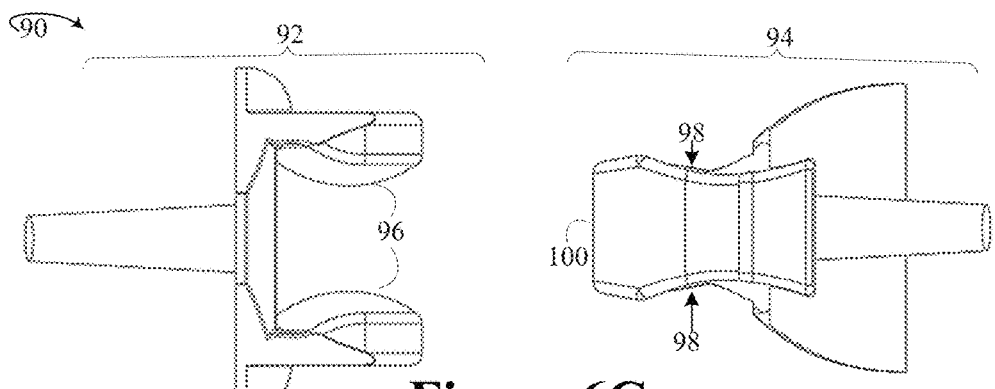
Figure 6D:
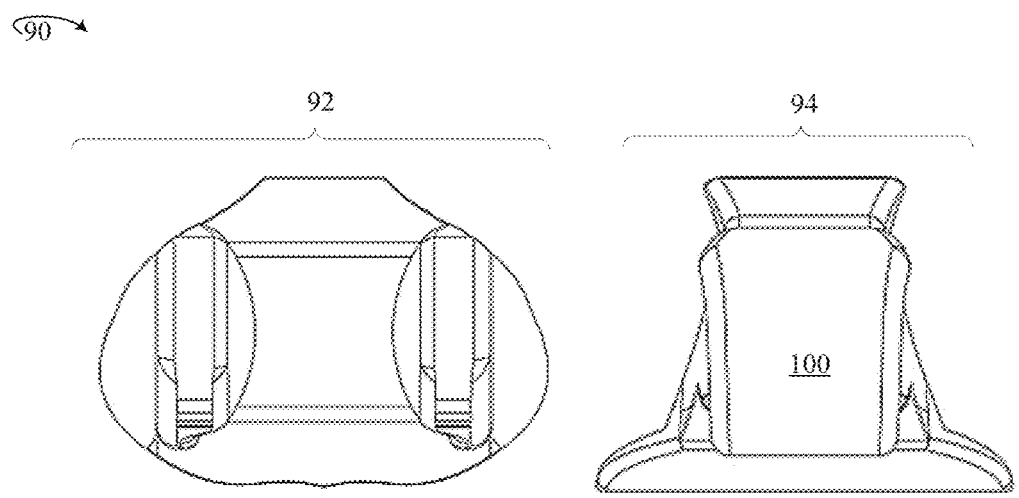
Figure 6E:
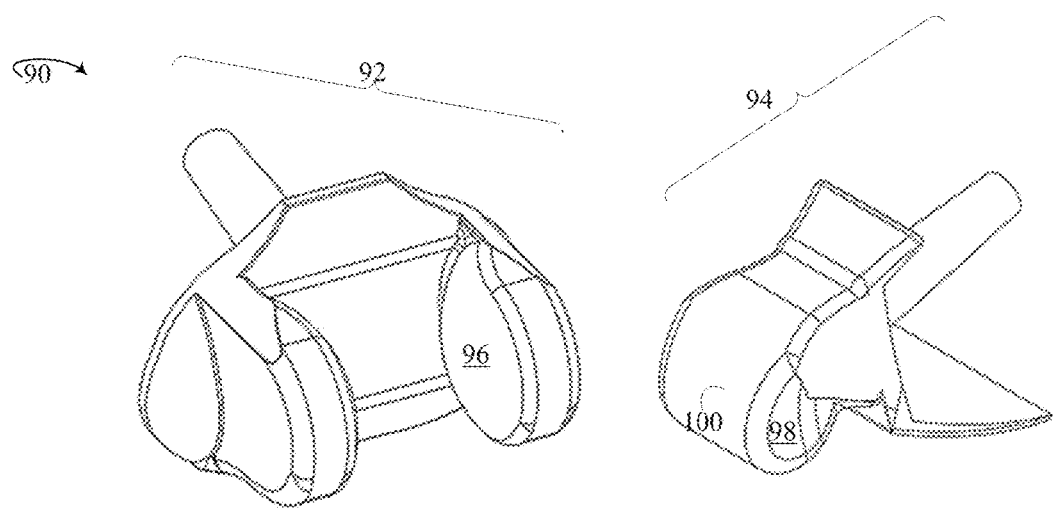

The distal fixation protrusion 84 of the distal fixation element 24 includes a rectilinear tapered shape with rounded edges and a rounded end as illustrated in FIGS. 5C and 5D.

The distal fixation protrusion 84 of the distal fixation element 24 includes a dorsal angle of approximately 80 degrees, relative to the distal fixation surface 26, and follows the medullary canal of the middle phalange (as implanted).

The distal fixation protrusion 84 includes two laterally located flanges 86 which extend laterally from the distal fixation protrusion 84 and distally from the distal fixation surface 26. In one embodiment, the flange forms an approximately triangular shape with one base affixed to the distal fixation protrusion 84 of the distal fixation element 24 and another base affixed to the distal fixation surface 26. In some instances, the flanges 86 provide anti-rotational support.

With reference to FIGS. 6A-6E, an example modular PIP prosthesis partially constrained mobile element 90 which is semi-constrained in lateral movement is illustrated. For example, a small degree of lateral movement is allowed, such as 2-4 degrees. The example modular PIP prosthesis partially constrained mobile element 90 is schematically illustrated in a side view of a distal portion 92 and a proximal portion 94, a palmar view of the distal portion 92 and the proximal portion 94, a dorsal view of the distal portion 92 and the proximal portion 94, a distal view of the distal portion 92 and proximal view of the proximal portion 94 view, and a perspective view of the distal portion 92 and the proximal portion 94, respectively. In one embodiment, the partially constrained mobile element 90 provides a small translation between the distal portion 92 and the proximal portion 94 during flexion, such as 1 mm For example, the proximal portion 94 slides relative to the distal portion 92 as the joint operates. Translation of the center of rotation during flexion brings the distal portion 92 and the proximal portion 94 closer and during extension further away. The shape of surface 100 that is semi-circular mediates this translation.

The distal portion 92 includes two lateral opposing partial semi-spherical shapes 96 oriented transverse to the center axis, which partially constrain the partially constrained mobile element 90 in a connected configuration with complementary indentations of partial semi-spherical shapes 98 in the proximal portion 94. In one embodiment the partial semi-spherical shapes 98 includes a slight oval shape to provide the translation. In another embodiment the partial semi-spherical shapes 98 are not perfectly concentric to shapes 96 in order to achieve adducting, abducting, and torsional twisting between portions 94 and 92. Distal portion 92 and the proximal portion 94 are connected prior to or during implantation. The connection is configured in a range of motion which exceeds normal range of motion due to the dorsal lessening of the semi-spherical indentation 98 of the proximal portion 94 as viewed in the palmar view.

The distal portion 92 includes a distal coupling element 56 represented as a tapered cylindrical shape which is dimensioned in an embodiment according the distal protrusion 56 and includes the mobile coupling surface 54. The distal portion 92 is manufactured of the same material as the distal portion 64 of the unconstrained mobile element 60, such as UHMWPE.

The proximal portion 94 includes a proximal coupling element 52 represented as a tapered cylindrical shape which is dimensioned in an embodiment according to the proximal protrusion 52 and the three proximal coupling surfaces 46, 48, and 50. The proximal portion 94 is manufactured of the same material as the proximal portion 62 of the unconstrained mobile element 60, such as cobalt-chromium (CoCr).

Figure 7:
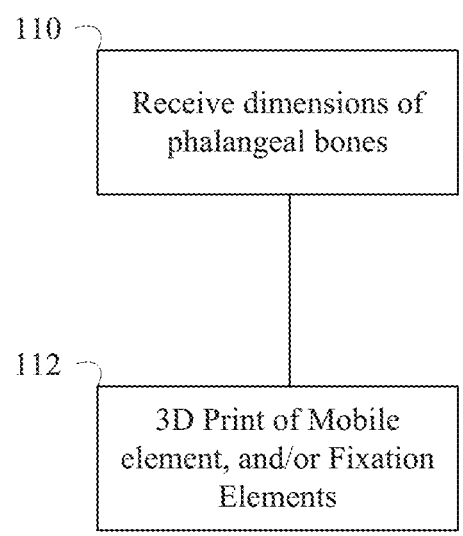

With reference to FIG. 7, a flowchart illustrates a construction of a modular interphalangeal joint. At 110, dimensions of phalange bones are received, such as one or more dimensions of a proximal phalange and a middle phalange. The received dimensions can be based on healthy bones or using a table converted to those of a healthy joint based on other data such as other bone measurements of a subject. The measurements can be based on one or more medical images.

At 112, a mobile element 12, a proximal fixation element 22, and/or a distal fixation element 24 are printed in three dimensions using three dimensional printing according to the received dimensions of interphalangeal bones.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An interphalangeal prosthesis, comprising:
   a mobile element which includes a proximal portion and a distal portion, and the proximal portion includes three proximal mobile coupling contiguous surfaces and a proximal mobile coupling protrusion, and the distal portion includes a distal coupling mobile surface and a distal mobile coupling protrusion, and the proximal portion and the distal portion are configured to move relative to each other primarily in an axis of rotation perpendicular to a plane that extends through the proximal mobile coupling protrusion, the three proximal mobile coupling contiguous surfaces, distal coupling mobile surface, and the distal mobile coupling protrusion in an implanted configuration;
   a proximal fixation element which couples to the three proximal mobile coupling contiguous surfaces and the proximal mobile coupling protrusion of proximal portion, and is configured to couple to a joint bone surface and a bone canal, wherein the proximal fixation element comprises a proximal fixation first surface, a proximal fixation second surface, and a proximal fixation third surface that are contiguous, and the proximal fixation first surface and the proximal fixation third surface are angled to the proximal fixation second surface, which are dimensioned to couple to a non-canal bone surface and a proximal opposing first coupling surface opposite the proximal fixation first surface, a proximal opposing second coupling surface opposite the proximal fixation second surface, and a proximal fixation opposing third coupling surface opposite proximal fixation third surface which are dimensioned to couple with the three proximal mobile coupling contiguous surfaces of the proximal portion of the mobile element; and
   a distal fixation element which couples to the distal coupling mobile surface and the distal mobile coupling protrusion, and is configured to couple to an opposing joint bone surface and a second bone canal.

2. The interphalangeal prosthesis of claim 1, wherein the proximal fixation first surface, the proximal fixation second surface, and the proximal fixation third surface couple are planar.

3. The interphalangeal prosthesis according to claim 1, wherein the proximal fixation element includes
   a proximal fixation protrusion extending from the proximal fixation second surface and dimensioned to be inserted inside bone, and a proximal opening into the fixation proximal protrusion from the proximal opposing second surface, and the proximal opening dimensioned to receive the proximal mobile coupling protrusion of the mobile element;
   wherein the proximal mobile coupling protrusion of the mobile element comprises a cruciform shape; and
   wherein the proximal opening comprises a complementary cruciform shape opening to the cruciform shape of the proximal mobile coupling protrusion of the mobile element.

4. The interphalangeal prosthesis according to claim 1, wherein the distal fixation element includes:
   a distal fixation surface, and a distal opposing coupling surface opposite the distal fixation surface, and the distal fixation surface is dimensioned to couple to a bone surface, and the distal opposing coupling surface is dimensioned to couple with the distal coupling mobile surface; and
   a distal fixation protrusion extending from the distal fixation surface and dimensioned to be inserted inside bone, and a distal opening into the distal fixation protrusion from the distal opposing coupling surface, and the distal opening dimensioned to receive the distal mobile protrusion of the mobile element.

5. The interphalangeal prosthesis according to claim 4, wherein distal fixation protrusion includes a tapered rectilinear volume with rounded edges, and flanges located laterally on a short side of the tapered rectilinear volume and affixed to the distal fixation protrusion and the distal fixation surface.

6. The interphalangeal prosthesis according to claim 1, wherein the distal fixation element and the proximal fixation element are comprised of different biocompatible materials.

7. The interphalangeal prosthesis according to claim 6, wherein the distal fixation element is comprised of titanium (Ti) and the proximal fixation element is comprised of cobalt-chromium (CoCr).

8. The interphalangeal prosthesis according to claim 1, wherein the fixation element comprises a distal fixation surface, and a distal opposing coupling surface opposite the distal fixation surface, and the distal fixation surface is dimensioned to couple to a bone surface, and the distal opposing coupling surface is dimensioned to couple with the distal coupling mobile surface; and
   wherein the proximal fixation first surface, the proximal fixation second surface, the proximal fixation third surface, and the distal fixation surface include roughened surfaces configured to couple to non-medullary canal bone surfaces.

9. The interphalangeal prosthesis according to claim 1, wherein proximal fixation protrusion includes a tapered rectilinear volume with rounded edges.

10. The interphalangeal prosthesis according to claim 1, wherein at least one of the mobile element, the proximal fixation element, or the distal fixation element are constructed of material layers by three dimensional printing.

11. The interphalangeal prosthesis according to claim 1, wherein the mobile element includes an unconstrained mobile element, and the unconstrained mobile element comprises the proximal portion, and the distal portion which are physically separated and made of different biocompatible materials dimensioned to a volume image of a healthy interphalangeal joint.

12. The interphalangeal prosthesis according to claim 11, wherein the the proximal portion includes cobalt-chromium (CoCr), and the distal portion includes ultra high molecular weight polyethylene (UHMWPE).

13. The interphalangeal prosthesis according to claim 1, wherein the mobile element comprises a partially constrained mobile element that is configured to provide a translation and rotation between the proximal portion and the distal portion during flexion-extension movements and constrained in lateral movement to less than four degrees.

14. An interphalangeal prosthesis, comprising: a mobile element which includes a proximal portion and a distal portion, and the proximal portion includes three proximal mobile coupling contiguous surfaces and a proximal mobile coupling protrusion, and the distal portion includes a distal coupling mobile surface and a distal mobile coupling protrusion, and the proximal portion and the distal portion are configured to move relative to each other primarily in an axis of rotation perpendicular to a plane that extends through the proximal mobile coupling protrusion, the three proximal mobile coupling contiguous surfaces, distal coupling mobile surface, and the distal mobile coupling protrusion in an implanted configuration;
 a proximal fixation element which couples to the three proximal mobile coupling contiguous surfaces and the proximal mobile coupling protrusion of proximal portion, and is configured to couple to a joint bone surface and a bone canal; and
 a distal fixation element which couples to the distal coupling mobile surface and the distal mobile coupling protrusion, and is configured to couple to an opposing joint bone surface and a second bone canal; and
 wherein the mobile element includes a constrained mobile element, and the constrained mobile element comprises a single integrated apparatus with a central portion, the proximal portion, and the distal portion, and the central portion joins the proximal portion and the distal portion and provides lateral support and rotation of the distal portion relative to the proximal portion.

15. The interphalangeal prosthesis according to claim 14, wherein the constrained mobile element is constructed using structural topological optimization (STO) operation utilizing force vector inputs replicating those found in healthy interphalangeal joint, structural topological optimization identifies material necessary to operate the single integrated apparatus which includes a hinge shape and removes one or more areas of structurally unnecessary material.

16. The interphalangeal prosthesis according to claim 14, wherein the constrained mobile element is constructed of a medical grade elastomer.

17. An interphalangeal prosthesis, comprising:
 a mobile element which includes a proximal portion and a distal portion, and the proximal portion includes three proximal mobile coupling contiguous surfaces and a proximal mobile coupling protrusion, and the distal portion includes a distal coupling mobile surface and a distal mobile coupling protrusion, and the proximal portion and the distal portion are configured to move relative to each other in an axis of rotation within one plane that extends through the proximal mobile coupling protrusion, the three proximal mobile coupling contiguous surfaces, the distal coupling mobile surface, and the distal mobile coupling protrusion;
 a proximal fixation element which couples to the three proximal mobile coupling contiguous surfaces and the proximal mobile coupling protrusion of proximal portion, and is configured to couple to a joint bone surface and a bone canal, wherein the proximal fixation element comprises three contiguous surfaces configured to couple to non-canal bone surfaces;
 a distal fixation element which couples to the distal coupling mobile surface and the distal mobile coupling protrusion, and is configured to couple to an opposing joint bone surface and a second bone canal; and
 wherein at least one of the mobile element, the proximal fixation element, and the distal fixation element are formed in layers using three dimensional (3D) printing.

\* \* \* \* \*